(12) United States Patent
Yamamoto et al.

(10) Patent No.: US 7,511,078 B2
(45) Date of Patent: Mar. 31, 2009

(54) ANTIALLERGIC AGENTS, DRUGS, FOODS, DRINKS OR COSMETICS CONTAINING THEM AND PROCESS FOR PRODUCING THE SAME

(75) Inventors: Taichi Yamamoto, Noda (JP); Tomoko Kanamori, Noda (JP); Fumio Yamaguchi, Noda (JP); Makoto Saito, Noda (JP); Ryohei Tsuji, Noda (JP); Akio Obata, Noda (JP)

(73) Assignee: Kikkoman Corporation, Noda-shi (JP)

( * ) Notice: Subject to any disclaimer, the term of this patent is extended or adjusted under 35 U.S.C. 154(b) by 227 days.

(21) Appl. No.: 10/312,504

(22) PCT Filed: Jun. 28, 2001

(86) PCT No.: PCT/JP01/05553

§ 371 (c)(1),
(2), (4) Date: Dec. 27, 2002

(87) PCT Pub. No.: WO02/00239

PCT Pub. Date: Jan. 3, 2002

(65) Prior Publication Data

US 2003/0138511 A1 Jul. 24, 2003

(51) Int. Cl.
*A61K 31/12* (2006.01)
*A61K 35/78* (2006.01)

(52) U.S. Cl. .................... 514/679; 424/777
(58) Field of Classification Search ............. 424/725
See application file for complete search history.

(56) References Cited

U.S. PATENT DOCUMENTS

| | | | | |
|---|---|---|---|---|
| 3,686,319 A | * | 8/1972 | Lafon | 568/306 |
| 4,279,930 A | * | 7/1981 | Hall et al. | 514/685 |
| 5,109,025 A | * | 4/1992 | Satoh et al. | 514/679 |
| 5,395,624 A | * | 3/1995 | Li et al. | 424/450 |
| 5,432,068 A | * | 7/1995 | Albertsen et al. | 800/274 |
| 5,445,816 A | * | 8/1995 | Li et al. | 424/62 |
| 5,665,367 A | * | 9/1997 | Burger et al. | 424/401 |
| 5,972,382 A | * | 10/1999 | Majeed et al. | 424/464 |
| 5,977,184 A | * | 11/1999 | Birdsall et al. | 514/685 |
| 6,113,955 A | * | 9/2000 | Deutz et al. | 426/52 |
| 6,300,369 B1 | * | 10/2001 | Ancira | 514/460 |
| 6,534,086 B1 | * | 3/2003 | Krumhar | 424/464 |
| 6,562,794 B1 | * | 5/2003 | Lanzendorfer et al. | 514/28 |

FOREIGN PATENT DOCUMENTS

| EP | 0 370 461 A2 | | 5/1990 |
|---|---|---|---|
| JP | 60-192555 A | | 1/1985 |
| JP | 63-218619 A | | 9/1988 |
| JP | 04-169526 A | | 6/1992 |
| JP | 11-035444 | * | 2/1999 |
| RU | 2058133 C1 | * | 4/1996 |
| WO | WO 87/05215 A1 | | 9/1987 |
| WO | WO 00/04175 A1 | | 1/2000 |

OTHER PUBLICATIONS

Yamaguchi et al. Cross-reaction of chalcone synthase and stilbene synthase overexpressed in *Escherichia coli*. FEBS Letters 460 (1999) 457-461.*
http://www.parenthood.com/articles.html?article_id=4256; Retrieved Jan. 30, 2006.*
AN 1992:530019-Zeitschrift fuer lebensmittel-Untersuchung und-Forschung, abstract 1992, 194(1), 29-32.*
Hoshino, Kaori et al., Shokuhin Eiseigaku Zasshi, vol. 39, No. 2, pp. 72-77, (1998).
Takeuchi, Ikuko et al., Kenkyu Hokokusho-Toyo Shokuhin Kogyo Tanki Daigaku, Toyo Shokuhin Kenkyusho, No. 15, pp. 74-78, (1983).
Laguna, Lidia et al., Physiologia Plantarum, vol. 105, No. 3, pp. 491-498, (1999).
Luque, P. et al., Archives of Biochemistry and Biophysics, vol. 317, No. 2, pp. 417-422, (1995).
Krause, M. et al, Z-Lebensm-Unters to Forsch, vol. 194, No. 1, pp. 29-32, (1992).
Hunt, G.M. et al., Phytochemistry, vol. 19, No. 7, pp. 1415-1420, (1980).
Chuda, Yoshihiro et al., J. Agric. Food Chem., vol. 46, No. 4, pp. 1437-1439, (1998).
Chuda, Yoshihiro et al., J. Argic. Food Chem, vol. 44, No. 8, pp. 2037-2039, (1996).
Maruta, Yoshihiko et al., J. Agric. Food Chem., vol. 43, No. 10, pp. 2592-2595, (1995).
Merfort, Irmgard, Phytochemistry, vol. 31, No. 6, pp. 2111-2113, (1992).
Rastrelli, Luca et al., Pharm. Biol., vol. 36, No. 5, pp. 315-319, (1998).
Agata, Isao et al., Phytochemistry, vol. 33, No. 2, pp. 508-509, (1993).
N. C. Cook et al.; Nutritional Biochemistry; vol. 7; pp. 66-76; 1996; XP002944448.

* cited by examiner

*Primary Examiner*—Brian-Yong S Kwon
(74) *Attorney, Agent, or Firm*—Birch, Stewart, Kolasch & Birch, LLP

(57) ABSTRACT

The present invention provides an antiallergic agent comprising, as an active ingredient, at least one of a tomato extract, tomato pericarp, naringenin chalcone or its derivatives, tricaffeoylquinic acid or its derivatives and dicaffeoylsuccinylquinic acid or its derivatives; a histamine-release inhibitor or a leukotriene-release inhibitor; and a medicament, food, drink or cosmetic comprising the antiallergic agent, the histamine-release inhibitor or the leukotriene-release inhibitor mentioned above; and a method for producing an antiallergic agent comprising extracting raw material tomato with a solvent.

5 Claims, 9 Drawing Sheets

ANTIALLERGIC AGENTS, DRUGS, FOODS, DRINKS OR COSMETICS CONTAINING THEM AND PROCESS FOR PRODUCING THE SAME

This application is the national phase under 35 U.S.C. § 371 of PCT International Application No. PCT/JP01/05553 which has an International filing date of Jun. 28, 2001, which designated the United States of America.

TECHNICAL FIELD

The present invention relates to tomato-based antiallergic agents, histamine-release inhibitors or leukotriene-release inhibitors, and their production process, and more particularly, to antiallergic agents, histamine-release inhibitors or leukotriene-release inhibitors comprising as an active ingredient naringenin chalcone or caffeic acid derivatives, medicaments, foods, drinks or cosmetics comprising the same, and a process for producing the same.

BACKGROUND ART

In recent years, the number of patients with allergic diseases such as bronchial asthma, pollinosis in adults and atopic dermatitis in children has been increasing, and these diseases have become a significant social problem. Currently one out of three people have some form of allergy, and allergies are even being referred to as a national disease. In general, there are four types of allergic reactions, which are anaphylaxis (type I), cytotoxic type (type II), alsas type (type III) and cell-mediated type (delayed type) (type IV). Pollinosis, which has particularly been an issue recently, is classified as a type I allergy. Also, atopic dermatitis is thought to be primarily due to a type I allergy reaction.

In type I allergies, IgE antibody, which is produced due to invasion of an allergen (antigen), binds to the Fc receptors on fat cells, and when a reinvading antigen binds to this IgE, chemical mediators (chemical substances) such as histamine and leukotriene are released from granules of the fat cells, which in turn either directly or indirectly cause an acute inflammatory reaction accompanied by symptoms such as asthma, rhinitis, sneezing, runny nose and itchy eyes. Thus, shutting down any of the above pathways could be effective in order to prevent type I allergic reactions.

Conventionally, extensive research has been conducted on pharmaceutical components having antiallergic action, and numbers of synthetic compounds have been reported to have such antiallergic action. For example, components with an activity to inhibit the release of histamine from fat cells or components with an activity to inhibit the release of leukotriene from macrophages (also referred to as leukotriene production inhibitory activity) can be expected to serve as antiallergic agents. However, there have been very few naturally occurring substances known to have an antiallergic activity. Moreover, there have been hardly any naturally occurring substances obtained that are safe and have an adequate antiallergic activity. Consequently, in the field of medicine in particular, there have been needs to search for compounds having an adequate antiallergic activity and to develop antiallergic agents.

The object of the present invention is to provide novel antiallergic agents, medicaments, foods, drinks or cosmetics comprising the same, and a process for producing the same.

The present inventors have conducted extensive and intensive studies to search for novel antiallergic agents by using histamine-release inhibitory activity as an indicator of efficacy in the treatment of allergic diseases. As a result, it was found that tomatoes contain components having an antiallergic activity, and that a fraction having an antiallergic activity is mainly contained in pericarps of tomatoes. In addition, the present inventors also found that the above fraction having an antiallergic activity consists of naringenin chalcone and the caffeic acid derivatives including tricaffeoylquinic acid and dicaffeoylsuccinylquinic acid, that these have histamine-release inhibitory activity, and that they are useful as antiallergic agents. Moreover, the antiallergic activity of these compounds was found to be more potent than that of other caffeic acid derivatives (such as caffeic acid or dicaffeoylquinic acid) known to have said activity.

DISCLOSURE OF THE INVENTION

The present invention relates to antiallergic agents, medicaments, foods, drinks and cosmetics comprising the same and production process for the same, as shown below.

(1) An antiallergic agent comprising a tomato extract as an active ingredient.

(2) A histamine-release inhibitor or a leukotriene-release inhibitor comprising a tomato extract as an active ingredient.

(3) An antiallergic agent comprising a tomato pericarp as an active ingredient.

(4) An antiallergic agent comprising naringenin chalcone or its derivatives as an active ingredient.

(5) A histamine-release inhibitor or a leukotriene-release inhibitor comprising naringenin chalcone or its derivatives as an active ingredient.

(6) An antiallergic agent comprising tricaffeoylquinic acid or its derivatives as an active ingredient.

(7) An antiallergic agent comprising dicaffeoylsuccinylquinic acid or its derivatives as an active ingredient.

(8) A histamine-release inhibitor comprising any of tricaffeoylquinic acid, dicaffeoylsuccinylquinic acid and their derivatives as an active ingredient.

(9) A leukotriene-release inhibitor comprising tricaffeoylquinic acid or its derivatives as an active ingredient.

(10) A medicament, food, drink and cosmetics comprising the antiallergic agent defined in any one of the above (1), (2), (3), (4), (6), and (7).

(11) A medicament, food, drink and cosmetics comprising the histamine-release inhibitor or the leukotriene-release inhibitor defined in any one of the above (2), (5), (8), and (9.).

(12) A method for producing an antiallergic agent comprising extracting raw material tomato with a solvent.

BEST MODE FOR CARRYING OUT THE INVENTION

Figure 1:
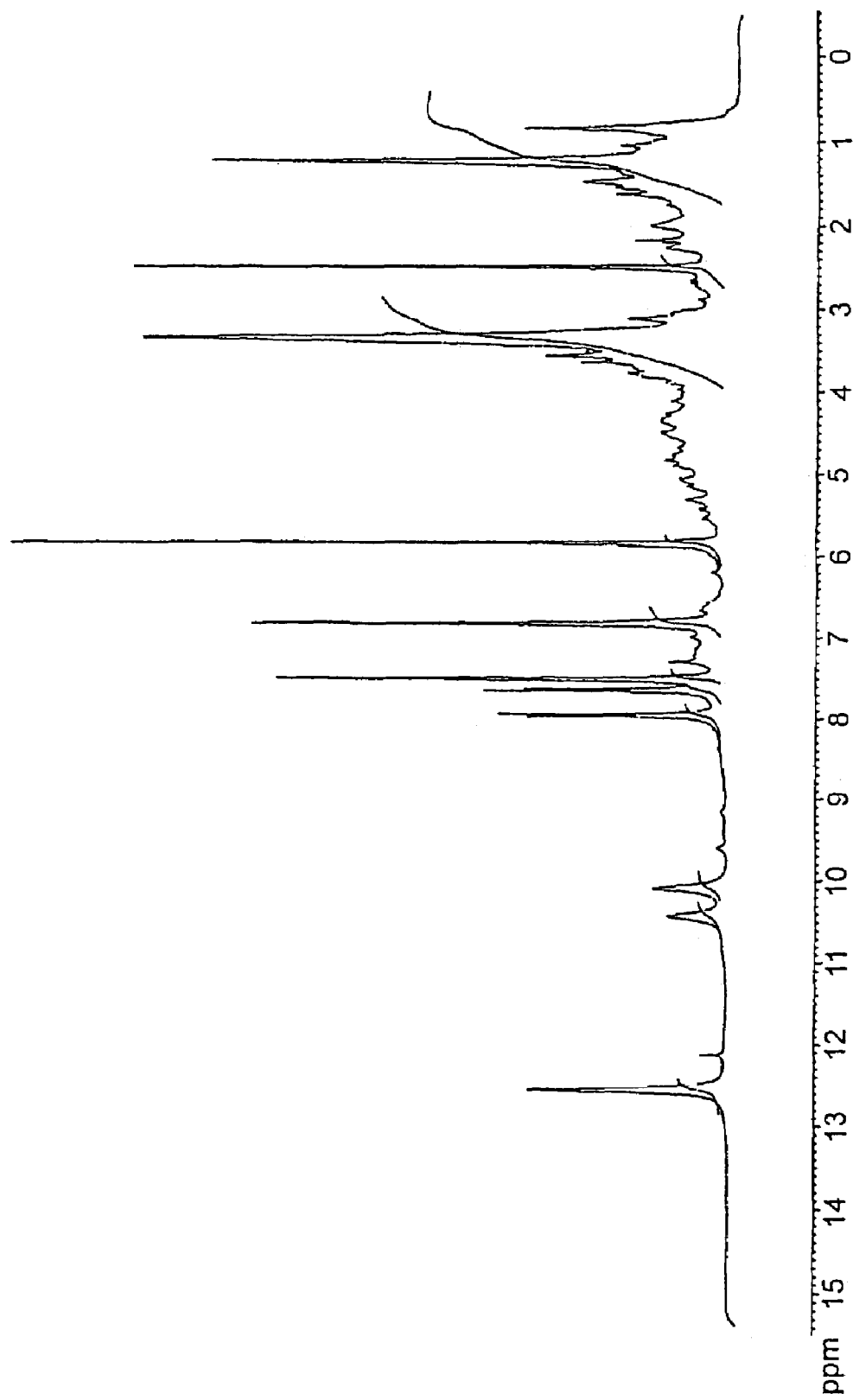
FIG. 1 shows a $^1$H-NMR spectrum of the histamine-release inhibiting component (naringenin chalcone) obtained in Examples 1 to 3.

The following provides a more detailed explanation of the present invention.

1. Antiallergic Agents Comprising a Tomato Extract as an Active Ingredient

The antiallergic agents of the present invention can be characterized by comprising a tomato extract as an active ingredient. The tomato extract can be obtained by, for example, extracting raw material tomatoes with a suitable solvent.

The raw material tomato to be extracted may be the whole tomato plant, as well as the fruit, pericarp, juice or any other arbitrary parts. A particularly preferred part is the pericarp because it contains a large amount of components having an antiallergic activity (hereinafter referred to as "antiallergic activity components"). In addition, the raw material tomato may also be residues obtained after squeezing the tomato fruit. The squeezed residues are particularly preferred since it contains a large amount of pericarp. There are no particular restrictions on the variety of the raw material tomato, and varieties typically available on the market and suitable for raw consumption or processing can be used.

In case that the raw material tomato contains a large amount of moisture, it is preferably used after drying in order to improve efficiency. More specifically, the moisture content is preferably reduced by, for example, drying either naturally or with hot air for 1 to 24 hours at 50 to 150° C. In addition, in order to increase extraction efficiency, the raw material tomato is preferably used after being finely ground. There are no particular restrictions on the grinding means, and examples of such include a method using a mortar, and methods using a crushing machine such as a whirling blender or a homogenizer. The raw material tomato is preferably ground to s size of 16 mesh or finer.

Raw material tomatoes suitable for extracting antiallergic activity components at high concentrations are those obtained by drying the tomato pericarps or squeezed tomato residues followed by crushing them.

There are no particular restrictions on the solvent used for extraction provided it is capable of extracting the antiallergic activity components, and ordinary polar solvents or amphiprotic solvent and so forth may be used. Examples of solvents that can be used include organic solvents, solvents containing organic solvents or mixed solvents of water and organic solvent.

Examples of organic solvents include low alcohols (specifically, ethanol, methanol, propanol and butanol), ethers (specifically, diethyl ether), halogenated carbons (specifically, chloroform), nitrites (specifically, acetonitrile), esters (specifically, ethyl acetate) and ketones (specifically, acetone) as well as hexane, dimethyl sulfoxide and dimethylformamide. From the viewpoint of working efficiency, ethanol, methanol and ethyl acetate are preferably used as the organic solvents. Two or more types of the organic solvents may be used in combination.

In view of extraction efficiency of the antiallergic activity components, a mixture of water and the organic solvent is particularly preferred for the solvent. Although there are no particular restrictions on the mixing ratios of water and the organic solvent, the organic solvent is preferably contained in a ratio of 20% or more, and particularly preferably in a ratio of 40 to 80%.

When considering that the tomato extract will ultimately be added to foods or cosmetics and so forth, ethanol is particularly preferable. In this case, in addition to 100% ethanol, aqueous alcohol, preferably 40 to 90% ethanol solution, and particularly preferably 50 to 70% ethanol solution, can be used.

There are no particular restrictions on the mixing ratios of the raw material tomato and the solvent during extraction, however, the solvent is preferably used in an amount of 2 to 10 times by weight, based on the weight of the raw material tomato, or 5 to 10 times by weight in view of the extraction procedures and efficiency. It is convenient to set a temperature for extraction to fall within the range of boiling point of the solvent at room temperature and under normal pressure, and it is particularly preferable to carry out extraction while heating and refluxing. When 60% ethanol is used as a solvent, the extraction temperature is preferably 40-70° C., and the extraction time is preferably within the range of 30 minutes to 24 hours.

Furthermore, prior to extraction with a solvent containing the organic solvent, impurities that are soluble in water can be removed by extracting the raw material tomato with cold water or hot water. In this case, the residues are recovered after water extraction and subjected to solvent extraction.

In the process of extraction, antiallergic activity components elute into the solvent. Since the antiallergic activity components are efficiently extracted by organic solvents, and particularly by alcohol-containing solvents, these components are expected to be present in a large amount, particularly in alcohol-soluble components of the tomato.

It is preferable to repeat the extraction step several times in order to improve extraction efficiency. Following extraction, solvent that contains the tomato extract is recovered by performing suction filtration and the like. As a result of the above procedure, a liquid tomato extract is obtained. Furthermore, the resulting fraction may be further purified by a synthetic adsorbent or ion exchange resin, etc. as necessary.

The resulting tomato extract can be used as an antiallergic agent, regardless of its state, whether it is in a state which contains a solvent or it is concentrated, or it is a dried product in which solvent has been removed from the extract. However, in view of storage properties and safety of the organic solvent, the tomato extract is preferably obtained in a dried state.

The antiallergic activity of fractions obtained at each step of the solvent extraction or resin purification can be measured using the inhibitory activity on the histamine-release from fat cells as an indicator. The measurement method is described in Example 2.

2. Antiallergic Agents Comprising a Tomato Pericarp as an Active Ingredient

In a different embodiment of the present invention, antiallergic agent of the present invention is characterized by comprising a tomato pericarp as its active ingredient. This is because the pericarp of the raw material tomato particularly contains a large amount of antiallergic activity components. The present inventors separated the squeezed tomato residues into pericarp and seeds, respectively, and measured their antiallergic activity with respect to the equal amounts of the resulting extracts. As a result, the antiallergic activity of the pericarp extract was about 5 to 10 times higher than the extract from the seeds.

Thus, tomato pericarp is extremely useful as an antiallergic agent. In this case, tomato pericarp means, for example, dried tomato fruit or those obtained by crushing the dried tomato fruit, squeezed tomato residue, dried squeezed tomato residue, and those obtained by crushing the dried squeezed tomato residue, and so forth. The tomato pericarp is preferably prepared in a form of granules, powder, tablets or blocks to facilitate use as an antiallergic agent. Antiallergic agents comprising a tomato pericarp as an active ingredient may also contain other components besides the pericarp. Examples of the other components include a solid carrier, a liquid carrier, an oil carrier, a preservative/a disinfectant, a fragrance, a flavoring agent and a colorant.

Furthermore, tomato tissues other than the pericarp such as pulp, seeds, etc. may also be contained in the antiallergic agent comprising the tomato pericarp as an active ingredient.

The present inventors have identified the components as shown below as the above-mentioned active components.

Namely, the antiallergic agents of the present invention comprise naringenin chalcone or its derivatives as their active ingredient. Naringenin chalcone (2',4',6',4-tetrahydroxychalcone) is a substance represented by the following formula (I).

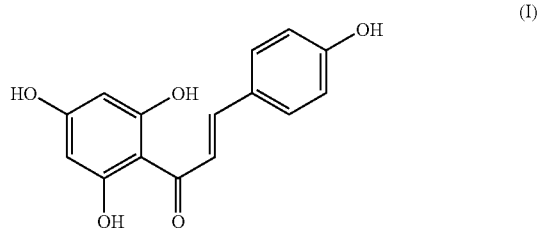

In addition, the antiallergic agents of the present invention comprise tricaffeoylquinic acid or its derivatives as their active ingredient. Tricaffeoylquinic acid is a substance represented by the following formula (II).

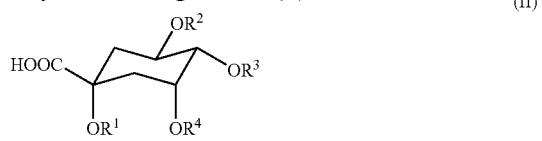

wherein one of $R^1$, $R^2$, $R^3$ and $R^4$ represents a hydrogen atom, while the remaining three represent a caffeoyl group represented by the following formula (III).

Formula (III):

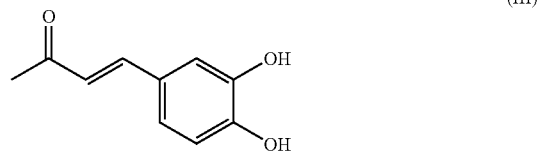

There are no particular restrictions on the position of the caffeoyl group in the tricaffeoylquinic acid provided it has an antiallergic activity, and three of $R^1$ through $R^4$ should be caffeoyl groups. Examples of the tricaffeoylquinic acid that can be used include 3,4,5-tricaffeoylquinic acid described in the examples. This compound is represented by the following formula (IV).

Formula (IV):

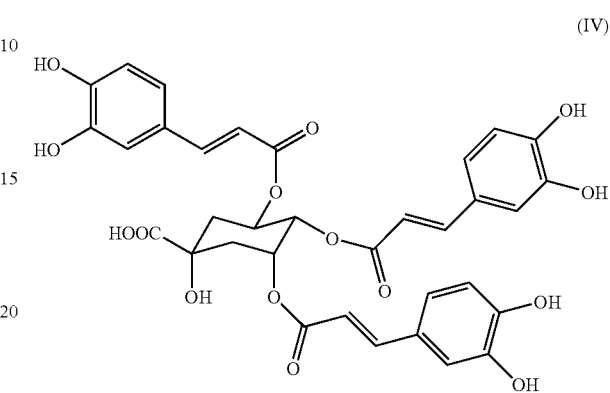

In a further different embodiment, antiallergic agents of the present invention comprises dicaffeoylsuccinylquinic acid or its derivatives as an active ingredient. Dicaffeoylsuccinylquinic acid is a substance represented by the following formula (V).

Formula (V):

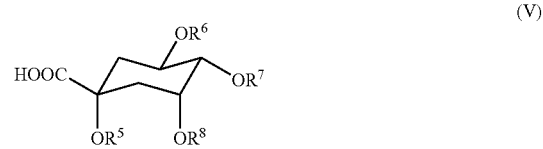

wherein one of $R^5$, $R^6$, $R^7$ and $R^8$ represents a hydrogen atom, one represents a succinyl group represented by the following formula (VI), and two represent caffeoyl groups represented by the above-mentioned formula (III).

Formula (VI):

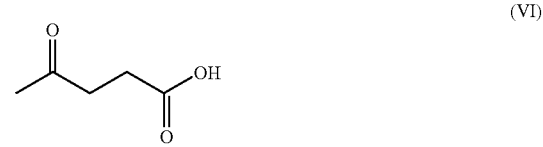

There are no particular restrictions on the positions of the caffeoyl groups or the succinyl group in the dicaffeoylsuccinylquinic acid provided it has an antiallergic activity, and two of $R^5$ through $R^8$ should be caffeoyl groups, and one should be a succinyl group. Examples of the dicaffeoylsuccinylquinic acid that can be used include 3,5-dicaffeoyl-4-succinylquinic acid described in the examples. This compound is represented by the following formula (VII).

Formula (VII):

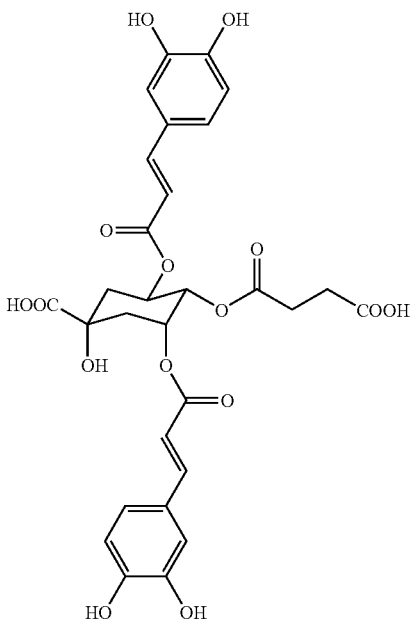

(VII)

Each of these compounds is a kind of derivatives of the caffeic acid represented by the following formula (VIII).

Formula (VIII):

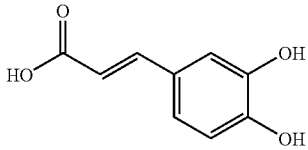

(VIII)

Caffeic acid has been known to have an antiallergic action. In addition, chlorogenic acid, dicaffeoylquinic acid and methyl chlorogenate are known to be caffeic acid derivatives having antiallergic actions (Japanese Provisional Patent Publication No. 192555/1985).

As indicated in the examples, naringenin chalcone, tricaffeoylquinic acid and dicaffeoylsuccinylquinic acid exhibit a superior activity of inhibiting histamine-release from fat cells. In addition, their activities are more potent than that of caffeic acid or dicaffeoylquinic acid. Thus, antiallergic agents comprising these compounds as an active ingredient are useful as preventive and therapeutic agents for various allergic diseases, anti-inflammatory agents or histamine-release inhibitors. Examples of the allergic diseases include atopic dermatitis, allergic rhinitis, pollinosis, allergic asthma, food allergies and inflammations.

Since the antiallergic agents of the present invention inhibit histamine-release from the fat cells in type I allergic reactions, they are useful in the prevention and treatment of atopic dermatitis, allergic rhinitis, pollinosis, allergic asthma and so forth caused thereby.

Furthermore, naringenin chalcone, tricaffeoylquinic acid or dicaffeoylsuccinylquinic acid may also include derivatives in which a portion of their structures are altered or modified, provided that they have an activity as antiallergic agents. Examples of these derivatives include pharmacologically acceptable salts, esters and pro-drugs.

There are no particular restrictions on the pharmacologically acceptable salts, and examples include salts with alkali metals (such as sodium and potassium), alkaline earth metals (such as magnesium and calcium), their hydroxides or carbonates, and alkali metal alkoxides (such as sodium methoxide and potassium t-butoxide). In addition, examples of salts include acid addition salts in which inorganic acid (such as hydrochloric acid, sulfuric acid or phosphoric acid) or organic acid (such as maleic acid, citric acid or fumaric acid) has been added, as well as addition salts of amines and addition salts of amino acids. Furthermore, hydrates of the above salts are also included in the salts referred to here.

There are no particular restrictions on the esters, provided they can be formed in an esterification reaction with alcohol or carboxylic acid. Examples of alcohols include methanol, ethanol, 1-propanol and 2-propanol, while examples of carboxylic acids include formic acid, acetic acid and lactic acid.

Pro-drugs refer to compounds that exhibit the action of antiallergic agents by converting themselves to naringenin chalcone, tricaffeoylquinic acid or dicaffeoylsuccinylquinic acid after being taken into the body. Compounds that have been converted to pro-drugs for the purpose of improving stability or adsorption or reducing adverse side effects and so forth are also included in the derivatives defined in the present invention.

3. Production Process of Antiallergic Agents

The above-mentioned tomato extract, naringenin chalcone, tricaffeoylquinic acid or dicaffeoylsuccinylquinic acid serving as an active ingredient of the antiallergic agents of the present invention may be produced by any method, and a variety of methods can be employed, including methods for purifying these compound from living organisms containing the same, chemical synthesis methods and semi-synthesis methods.

Naringenin chalcone, tricaffeoylquinic acid or dicaffeoylsuccinylquinic acid can be extracted from plants such as citrus fruits and vegetables, and more specifically tomato and *Chrysanthemum coronarium*, using a solvent containing organic solvent. In case of purifying naringenin chalcone or tricaffeoylquinic acid from tomato, 60% ethanol are added in a volume of 10 times as much to tomato pericarp or squeezed residue, extraction is carried out for 3 hours in warm water bath kept at 60° C. An extract containing naringenin chalcone and tricaffeoylquinic acid is obtained. This extract is subjected to high-performance liquid chromatography. After collecting the fractions that exhibit histamine-release inhibitory activity, the structures of the compounds contained in each fraction are confirmed. As a result, naringenin chalcone or tricaffeoylquinic acid can be purified.

Dicaffeoylsuccinylquinic acid can be purified from *Chrysanthemum coronarium* being freeze-dried and crushed, in a similar manner.

Furthermore, the antiallergic agents of the present invention are not limited to those containing only purified active ingredient, but may also be crudely purified products containing naringenin chalcone, tricaffeoylquinic acid or dicaffeoylsuccinylquinic acid.

Further, pharmacologically acceptable salts can be produced by reacting alkali metal, alkaline earth metal, alkali metal alkoxide, inorganic acid or organic acid with naringenin chalcone, tricaffeoylquinic acid or dicaffeoylsuccinylquinic acid. Esters can be produced by reacting alcohol or carboxylic acid with naringenin chalcone, tricaffeoylquinic acid or dicaffeoylsuccinylquinic acid in the presence of an acid catalyst.

4. Use of Antiallergic Agents of the Present Invention

The antiallergic agents of the present invention comprise a tomato extract or a tomato pericarp, and more specifically, naringenin chalcone, tricaffeoylquinic acid or dicaffeoylsuccinylquinic acid as their active ingredient. As is indicated in the examples, the antiallergic agents of the present invention exhibit an activity of inhibiting histamine-release from the fat cells or leukotriene-release from the macrophages. Thus, the antiallergic agents of the present invention are useful as preventive or therapeutic agents against various allergic diseases, as anti-inflammatory agents, or as histamine-release inhibitors or leukotriene-release inhibitors. Examples of allergic diseases include allergic rhinitis caused by pollen, mites or house dust, allergic dermatitis, food allergies caused in response to specific foods such as milk or eggs, allergic bronchial asthma and inflammations. The antiallergic agents of the present invention are useful for the prevention and treatment of allergic diseases caused by type I allergic reactions in particular.

The antiallergic agents of the present invention can be used as medicaments, foods, drinks or cosmetics having an antiallergic activity, anti-inflammatory activity, histamine-release inhibiting activity or leukotriene-release inhibiting activity, either directly or by adding to these products.

The antiallergic agents of the present invention may be used alone for medicaments, foods, drinks or cosmetics, or they may be used in combination with other antiallergic agents. Moreover, mixtures of at least two types of naringenin chalcone, tricaffeoylquinic acid and dicaffeoylsuccinylquinic acid may also be the antiallergic agents of the present invention.

A. Medicaments

The antiallergic agents of the present invention can be used as medicaments by formulating a tomato extract or a tomato pericarp by itself, or the above purified compounds by themselves, or by formulating these with a known pharmaceutical carrier into preparations. The antiallergic agents of the present invention can be prepared in a form of oral preparations including tablets, granules, powders and syrups, and in a form of parenteral preparations including suppositories and external preparations. There are no particular restrictions on the pharmaceutical carriers, and examples include solid carriers (such as starch, lactose and carboxymethyl cellulose), liquid carriers (such as distilled water, an aqueous D-glucose, ethanol, propylene glycol, etc.) and oil carrier (such as various animal and plant oils, white Vaseline and paraffin).

The above medicaments can be used for humans and animals other than humans (such as pets and livestocks). Although the dose of the above medicaments should be suitably determined according to the symptoms, sex, age of the patients who will use them, they could be administered, for example, in an amount of about 0.1-1000 mg per day per person.

B. Foods and Drinks

The antiallergic agents of the present invention can be used by themselves for foods and drinks having an antiallergic activity, anti-inflammatory activity, histamine-release inhibitory activity or leukotriene-release inhibitory activity. In addition, the above activity can be imparted to foods and drinks by adding the antiallergic agents of the present invention to foods and drinks such as tomato juice or tomato puree.

There are no particular restrictions on foods and drinks to which the antiallergic agents of the present invention could be added, and examples include meats, processed vegetables, prepared entrees, dairy products, confections, breads, soft drinks, fruit juices and alcoholic beverages. There is no specific formulation of the antiallergic agents of the present invention based on the food.

In addition, the antiallergic agents of the present invention may be mixed with other food materials and prepared into a form of granules, powders, tablets or blocks and so forth to serve as food materials, health foods and so forth. Examples of other food materials include sugars, edible proteins, alcohols, vitamins, thickened polysaccharides, amino acids, calcium salts, pigments, fragrances and preservatives.

C. Cosmetics

The antiallergic agents of the present invention can be added to cosmetics to impart an antiallergic activity, anti-inflammatory activity, histamine-release inhibitory activity or leukotriene-release inhibitory activity to the cosmetics. There are no particular restrictions on the kinds of cosmetics, and examples include skin lotion, facial cream, milky lotion, foundation, lipstick, hair spray, hair tonic, hair growing agent, toothpaste, mouthwash, shampoo and rinse.

In preparation of cosmetics, materials normally used as cosmetic raw materials can be suitably blended such as fats and oils including vegetable oils, waxes including lanolin and beeswax, hydrocarbons, fatty acids, higher alcohols, various surfactants, pigments, fragrances, vitamins, plant/animal extracts, ultraviolet ray absorbers, antioxidants and preservatives.

5. Histamine-Release Inhibitors of the Present Invention

As indicated in Examples, tomato extract, naringenin chalcone, tricaffeoylquinic acid and dicaffeoylsuccinylquinic acid exhibit histamine-release inhibitory activity, therefore, they are useful as histamine-release inhibitors.

Thus, the above compounds and so forth can be used either by themselves or by adding to medicaments, foods, drinks or cosmetics, for the prevention and treatment of diseases for which inhibition of histamine-release is effective. The above compounds and so forth may be used alone as the active ingredient of a medicament, or in combination of two or more kinds.

The naringenin chalcone, tricaffeoylquinic acid and dicaffeoylsuccinylquinic acid may include derivatives in which a portion of their structure has been altered or modified provided that they have activity as histamine-release inhibitors. Examples of derivatives of naringenin chalcone include pharmacologically acceptable salts, esters or pro-medicaments. Specific derivatives are as described in the previous section on antiallergic agents.

6. Leukotriene-Release Inhibitors of the Present Invention

As indicated in Examples, tomato extract, naringenin chalcone, tricaffeoylquinic acid and dicaffeoylsuccinylquinic acid exhibit leukotriene-release inhibitory activity, therefore, they are useful as leukotriene-release inhibitors (also referred to as leukotriene-production inhibitors).

Thus, the above compounds and so forth can be used either by themselves or by adding to medicaments, foods, drinks or cosmetics for the prevention and treatment of diseases for which inhibition of leukotriene activity is effective. The above compounds and so forth may be used alone as the active ingredient of a medicament, or in combination of two or more kinds.

The naringenin chalcone and tricaffeoylquinic acid may include derivatives in which a portion of their structure has been altered or modified provided that they have activity as leukotriene-release inhibitors. Examples of derivatives of naringenin chalcone include pharmacologically acceptable salts, esters or pro-medicaments. Specific derivatives are as described in the previous section on antiallergic agents.

EXAMPLES

The following shows examples of production methods of the antiallergic agents of the present invention comprising tomato extract and so forth as their active ingredient, histamine-release inhibition tests, and the production of medicaments, foods, drinks and cosmetics comprising antiallergic agents of the present invention.

Example 1

Example 1-1

Preparation of Tomato Extract (1) 20 g of squeezed and dried tomato residue were crushed with a mixer, and then, 200 ml of water was added thereto and the mixture was heated under reflux at 60° C. for carrying out water extraction to remove impurities. Subsequently, the extraction residue was collected and subjected to additional extraction by adding 200 ml of 60% ethanol as a solvent and by heating under reflux at 70° C. After filtering the resulting extract solution, the filtrate was concentrated under reduced pressure and freeze-dried, to give 812 mg of tomato extract powder (Tomato Extract 1).

(2) In the same manner as in the above (1), except for using 60% methanol as a solvent, 753 mg of tomato extract powder were obtained (Tomato Extract 2).

(3) In the same manner as in the above (1), except for using 60% ethyl acetate as a solvent, 625 mg of tomato extract powder were obtained (Tomato Extract 3).

Example 1-2

Preparation of Tomato Extract (1) 100 g of tomato paste was separated by centrifugation, and the resultant residue was collected. The resulting precipitates were freeze-dried, and 80 ml of ethanol and added thereto for extraction, and the extract was dried under reduced pressure to give 800 mg of extract powder (Tomato Extract 4).

(2) 300 g of raw edible tomatoes were crushed with a juicer and then, subjected to centrifugation to collect the residue. The resulting residue was freeze-dried and 150 ml of ethanol was added thereto for extraction and the extract was dried under reduced pressure to give 1.94 g of extract (Tomato Extract 5).

Example 1-3

Purification of Naringenin Chalcone

Figure 2:
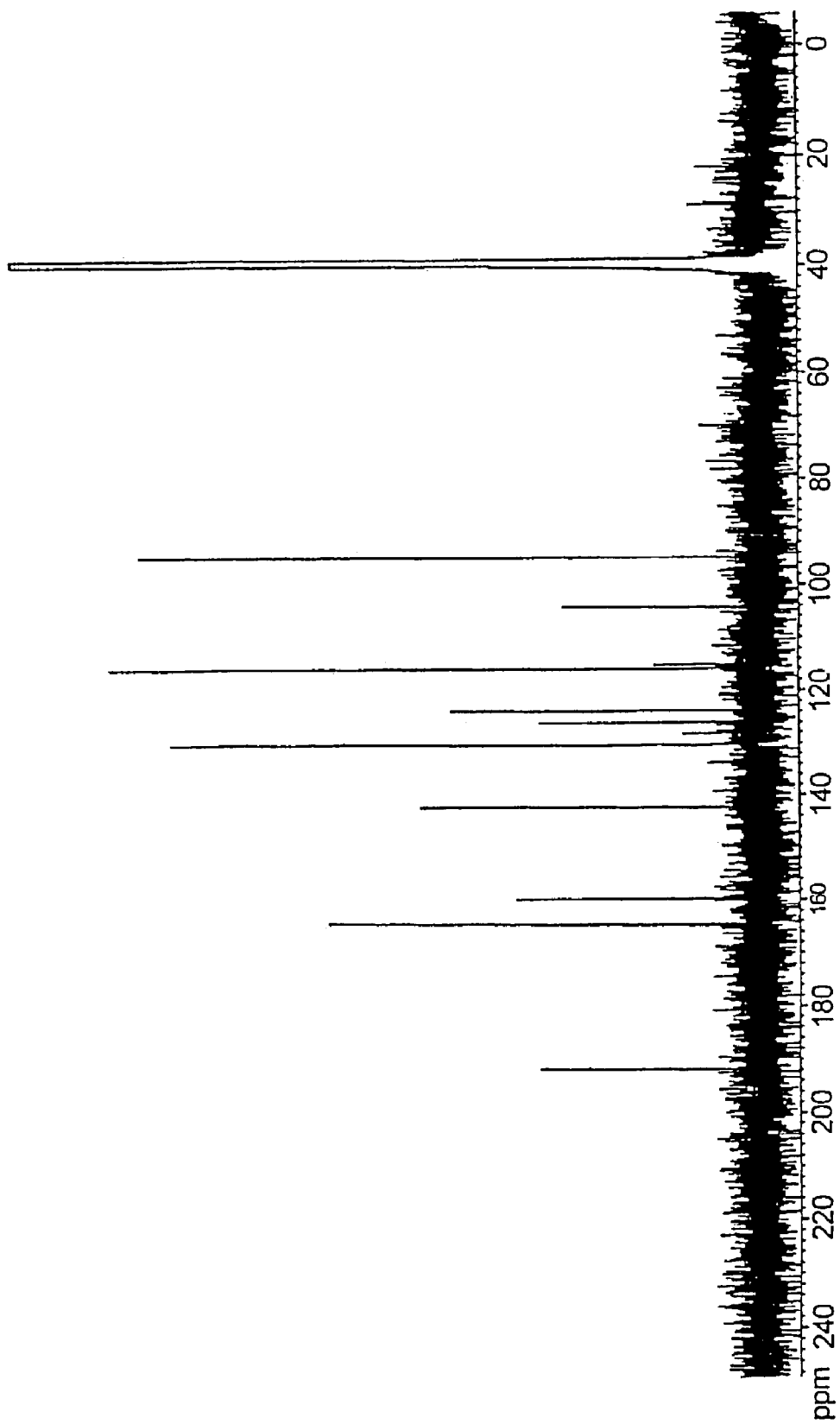
FIG. 2 shows a $^{13}$C-NMR spectrum of the histamine-release inhibiting component (naringenin chalcone) obtained in Examples 1 to 3.
Figure 3:
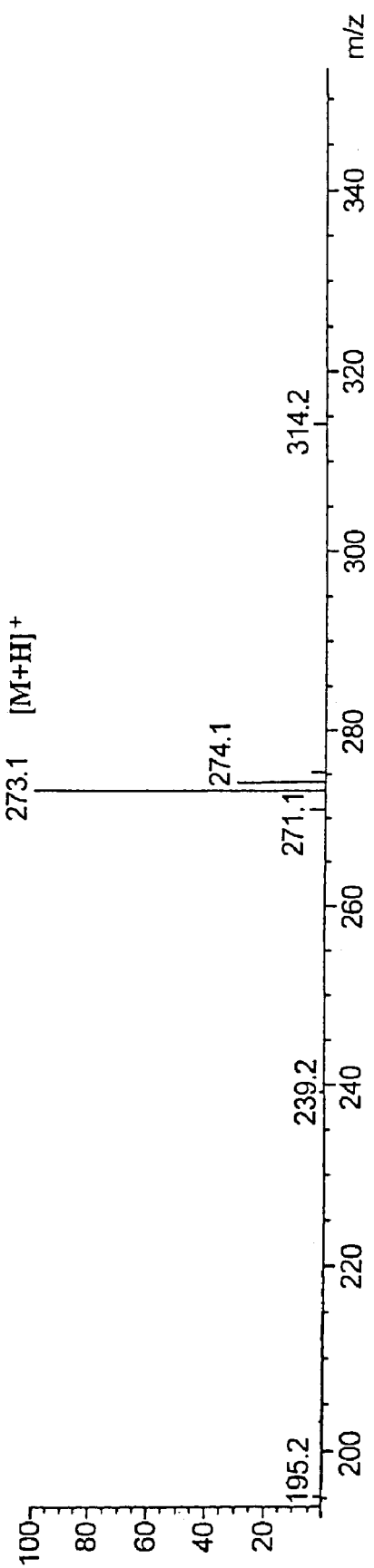
FIG. 3 shows a LC-MS of the histamine-release inhibiting component (naringenin chalcone) obtained in Examples 1 to 3.

Tomato pericarp was extracted with 60% ethanol in warm water bath at 60° C. for 2 hours. The extract was filtered, and the resulting filtrate was concentrated under reduced pressure. It was fractionated by high-performance liquid chromatography (column: SHISEIDO CAPCELL PAK C18 15 mm diameter×250 mm; eluent: acetonitrile containing 0.1% trifluoroacetic acid/water=40/60) to give a histamine-release inhibitory component. The above component was identified by utilizing LC-MS, NMR and so forth. The $^1$H-NMR spectrum is shown in FIG. 1, the $^{13}$C-NMR spectrum is shown in FIG. 2, and LC-MS is shown in FIG. 3. Said compound was confirmed to be naringenin chalcone based on the above results. Furthermore, the histamine-release inhibiting activity of the fractions obtained at each stage of purification was measured according to the method described in Example 2.

Example 1-4

Purification of Tricaffeoylquinic Acid

Tomato pericarp was extracted with 60% ethanol in warm water bath at 60° C. for 2 hours. The extract was filtered and the resulting filtrate was concentrated under reduced pressure followed by freeze-drying to give an extract of tomato pericarp. This was then dissolved in 20% ethanol and the mixture was subjected to column chromatography using YMC gel ODS-AM120-S50 (YMC Co., Ltd.), and the component that was eluted with 30% ethanol solution was collected.

This was then further concentrated under reduced pressure and fractionated by high-performance liquid chromatography (column: SHISEIDO CAPCELL PAK C18 15 mm diameter×250 mm; eluent: acetonitrile containing 0.1% trifluoroacetic acid/water=28/72) to obtain a compound having histamine-release inhibitory activity.

Figure 4:
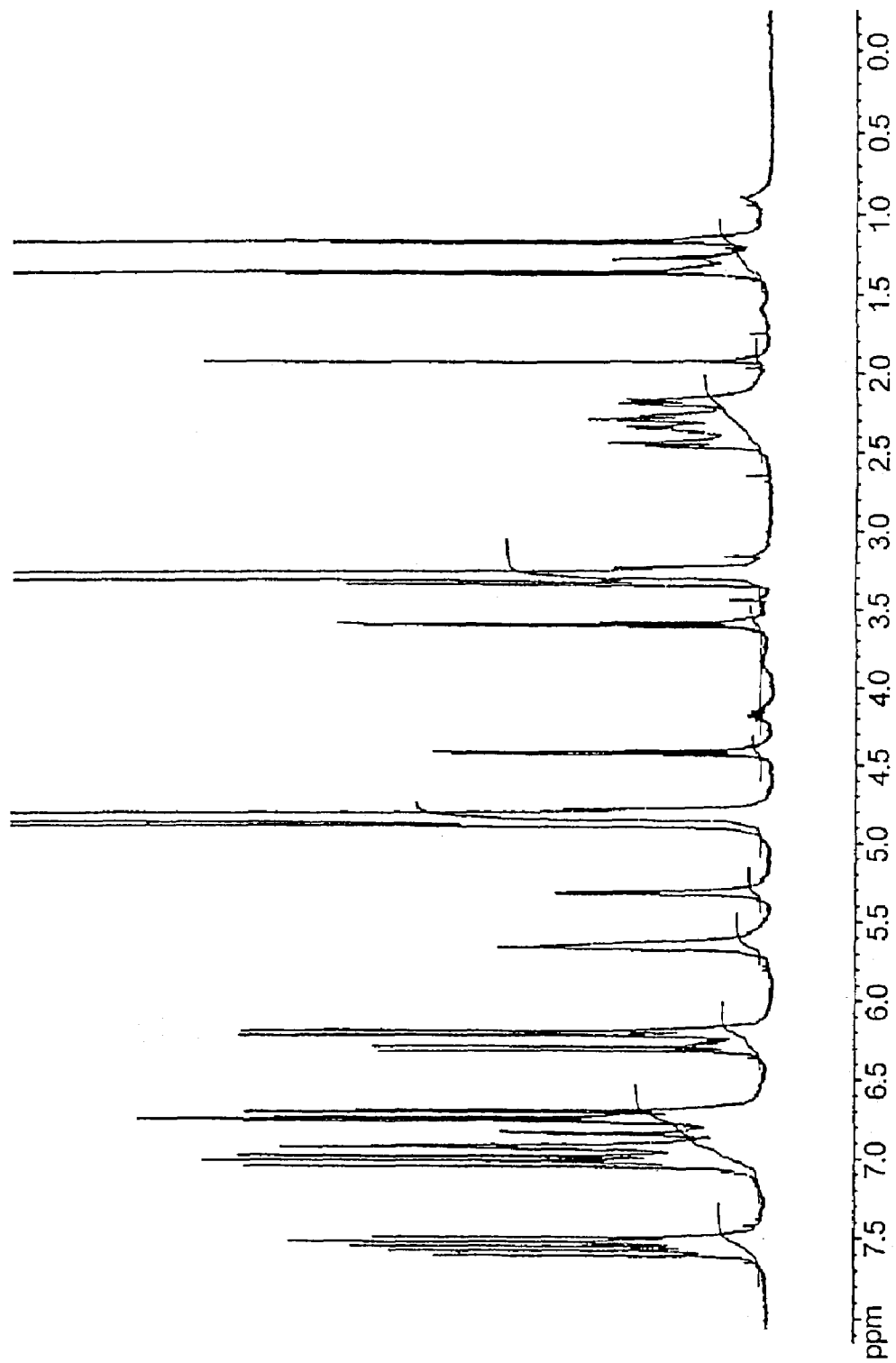
FIG. 4 shows a $^1$H-NMR spectrum of the compound with the histamine-release inhibiting activity (tricaffeoylquinic acid) obtained in Examples 1 to 4.
Figure 5:
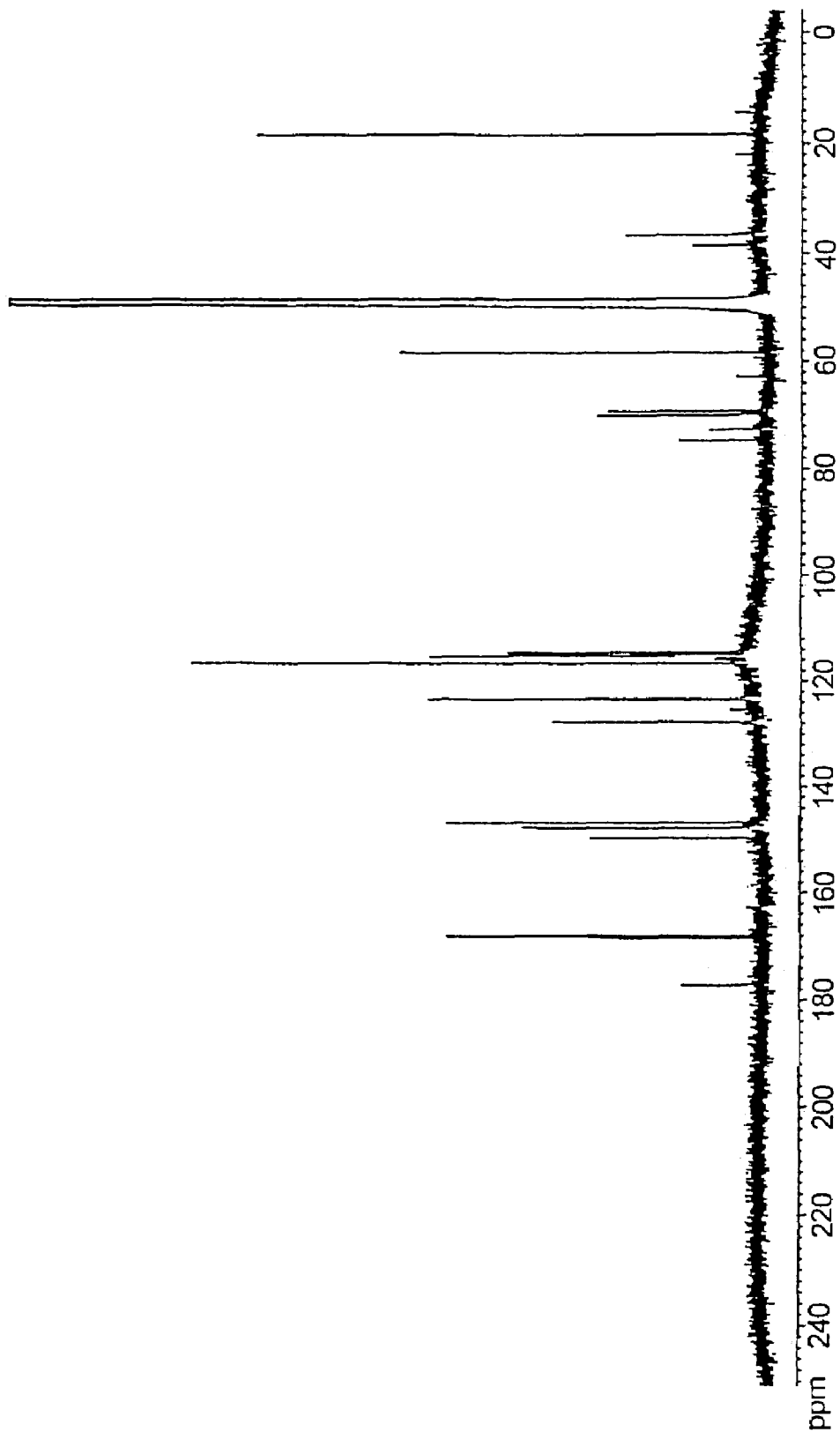
FIG. 5 shows a $^{13}$C-NMR spectrum of the compound with the histamine-release inhibiting activity (tricaffeoylquinic acid) obtained in Examples 1 to 4.
Figure 6:
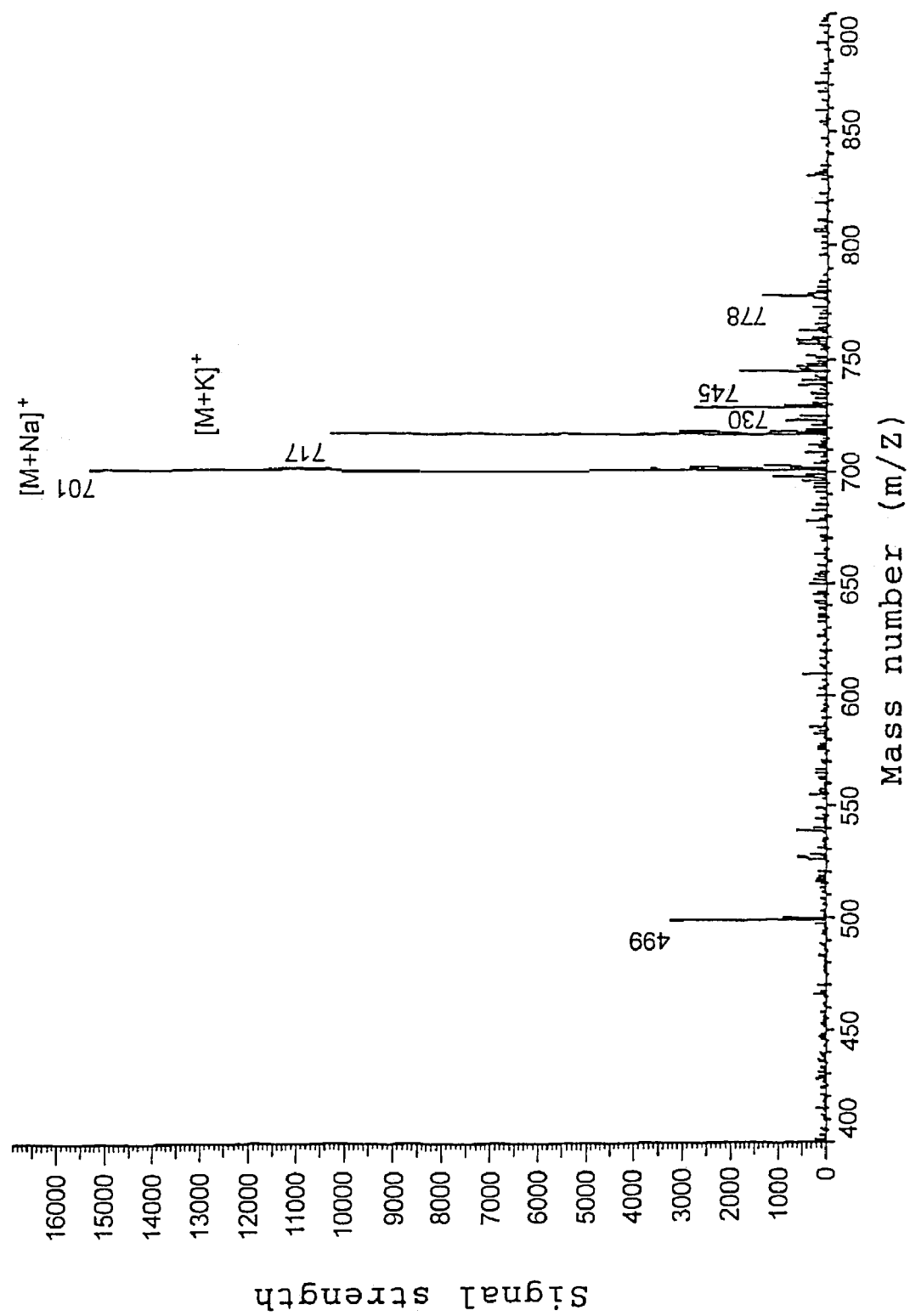
FIG. 6 shows a LC-MS of the compound with the histamine-release inhibiting activity (tricaffeoylquinic acid) obtained in Examples 1 to 4.

Next, said compound was identified using LC-MS, NMR and so forth. The $^1$H-NMR spectrum is shown in FIG. 4, the $^{13}$C-NMR spectrum is shown in FIG. 5, and LC-MS (Hitachi Science Systems, Techno Research Center) is shown in FIG. 6.

Said compound was confirmed to be 3,4,5-tricaffeoylquinic acid based on the above results. Furthermore, the histamine-release inhibitory activity of the fractions obtained at each stage of purification was measured according to the method described in Example 2.

Example 1-5

Purification of Dicaffeoylsuccinylquinic Acid

Dicaffeoylsuccinylquinic acid was purified with reference to the method described in the literature (Chuda et al., J. Agric. Food Chem. 46; 1437-1439, 1998).

Initially, *Chrysanthemum coronarium* was freeze-dried and crushed, and added thereto 60% ethanol. Extraction was carried out in a warm water bath at 50° C. for 2 hours. After filtering the extract and concentrating the resulting filtrate under reduced pressure, a compound was purified that had histamine-release inhibitory activity using high-performance liquid chromatography (column: SHISEIDO CAPCELL PAK C18 15 mm diameter×250 mm; eluent: acetonitrile containing 0.1% trifluoroacetic acid/water=23/77). Said compound was confirmed to be 3,5-dicaffeoyl-4-succinylquinic acid using LC-MS and so forth.

Example 2

Measurement of Histamine-Release Inhibiting Activity from Rat Fat Cells (1) Measurement of histamine-release inhibiting activity from rat fat cells was carried out according to the following method with respect to Tomato Extracts 1 to 3, naringenin chalcone and tricaffeoylquinic acid. The measurement results are shown in Table 1.

Cells were collected from the abdominal cavity of rats immediately after being sacrificed by exsanguinations using heparin-containing fat cell buffer (composition: 0.150 M NaCl, 3.7 mM KCl, 3.0 mM $Na_2HPO_4$, 3.5 mM $KH_2PO_4$, 0.9 mM $CaCl_2$, 5.6 mM D-glucose, 0.1% (w/v) gelatin) (Lectures on Experimental Biopharmacology, Vol.12, Inflammations and Allergies II, edited by Kazuo Ohuchi, published by Hirokawa Publishing, 1993, page 372). After washing the cells, the above heparin-containing fat cell buffer was added to a concentration of 2.0×10⁵ cells/ml, and this was used as the cell suspension.

Meanwhile, 3 mg of tomato extract were dissolved in 1 ml of 1% dimethyl sulfoxide (DMSO) and used as a sample solution. Further, the naringenin chalcone obtained in Example 1-3, and ketotifen fumarate, which is known to have an antiallergic activity, were respectively dissolved in the heparin-containing fat cell buffer containing 0.15% DMSO (final concentration), and the tricaffeoylquinic acid obtained in Example 1-4, and caffeic acid, which is known to have an antiallergic activity, were respectively dissolved in heparin-containing fat cell buffer containing 0.08% ethanol (final concentration), and each of these were used as sample solutions having concentrations of 25-250 μg/ml.

80 μl of the above cell suspension were added to 20 μl of the sample solution and the mixture was incubated at 37° C. for 10 minutes. Subsequently, 20 μl of Compound 48/80 (5 μg/ml) were added as histamine-degranulation inducer, and the mixture was incubated for 10 minutes. After the mixture was cooled with ice, it was separated by centrifugation (1,500×g, 5 minutes, 4° C.), and the free histamine in the supernatant was measured by high-performance liquid chromatography equipped with a fluorescent detector.

Histamine-release inhibiting activity was calculated from the measured histamine values using calculation formula (1) shown below.

$$\text{Histamine-release inhibition rate (\%)} = (1-(S-B)/(C-B)) \times 100 \quad (1)$$

B: Amount of histamine released from control cells in the absence of inducer
C: Amount of histamine released from cells in the presence of inducer
S: Amount of histamine released from cells in the presence of test sample and inducer

TABLE 1

| Samples | Concentration (μg/ml) | Inhibition rate (%) | IC$_{50}$ |
|---|---|---|---|
| Tomato Extract 1 | 200 | 79.8 | |
|  | 50 | 6.9 | |
| Tomato Extract 2 | 200 | 86.3 | |
| Tomato Extract 3 | 200 | 64.3 | |
| Tomato Extract 4 | 500 | 92.2 | |
|  | 167 | 25.8 | |
| Tomato Extract 5 | 1667 | 99.3 | |
|  | 500 | 34.3 | |
| Naringenin chalcone | 200 | 82.0 | About 70 μg/ml |
|  | 75 | 53.9 | |
|  | 50 | 37.6 | |
|  | 25 | 28.2 | |
| Tricaffeoylquinic acid | 75 | 93.2 | About 25 μg/ml |
|  | 25 | 54.1 | |
| Caffeic acid | 250 | 50.1 | About 250 μg/ml |
| Ketotifen fumarate | 250 | 49.4 | About 250 μg/ml |
|  | 75 | 13.1 | |
|  | 25 | 0.0 | |

As is clear from the results shown in Table 1, tomato extract was determined to have an extremely high histamine-release inhibiting activity. In addition, their activities were more potent than that of the known antiallergic agent, ketotifen fumarate. Naringenin chalcone exhibited a histamine-release inhibiting activity that was more potent than the known antiallergic agent, ketotifen fumarate. Tricaffeoylquinic acid exhibited an extremely high histamine-release inhibiting activity in a small amount. On the basis of the above, tomato extract, naringenin chalcone and tricaffeoylquinic acid were indicated as being useful as antiallergic agents or histamine-release inhibitors.

In addition, in the case of comparing with the known antiallergic agent, ketotifen fumarate, the IC$_{50}$ value (50% inhibition rate) of naringenin chalcone was about 70 μg/ml, and the IC$_{50}$ value (50% inhibition rate) of tricaffeoylquinic acid was about 25 μg/ml, while the IC$_{50}$ values of caffeic acid and ketotifen fumarate were about 250 μg/ml. This indicates that the activity of naringenin chalcone is roughly 3.5 times as high, and that the activity of tricaffeoylquinic acid is roughly 10 times as high as that of the known agents.

Figure 7:
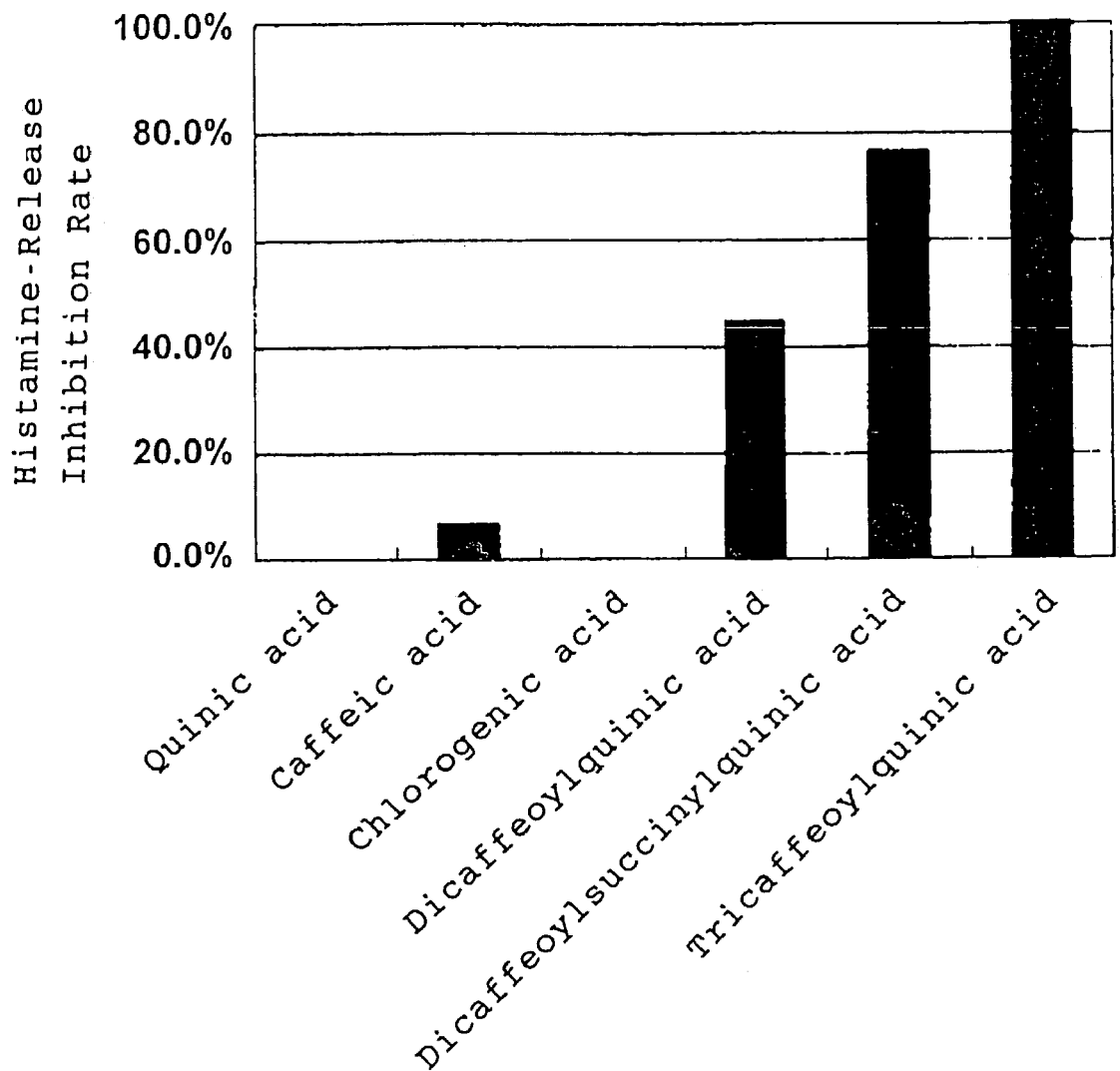
FIG. 7 shows results of measurements on the histamine-release inhibiting activity described in Example 2 (2).

(2) Next, evaluations were also made on caffeic acid and quinic acid, which are the components of tricaffeoylquinic acid and on the caffeic acid derivatives such as chlorogenic acid, dicaffeoylquinic acid and dicaffeoylsuccinylquinic acid. As a result of evaluations using the sample solutions having concentrations of 100 μg/ml each, quinic acid and chlorogenic acid did not inhibit histamine-release, as shown in FIG. 7. In addition, histamine-release inhibiting activity was determined to be more potent in the order of caffeic acid followed by dicaffeoylquinic acid, while dicaffeoylsuccinylquinic acid and tricaffeoylquinic acid exhibited a significantly high activity.

(3) As described above, since tricaffeoylquinic acid and dicaffeoylsuccinylquinic acid exhibit a high histamine-release inhibiting activity even in a small amount, these compounds were clearly confirmed to be useful as antiallergic agents or histamine-release inhibitors.

Example 3

Measurement of Leukotriene B$_4$—Release Inhibiting Activity

Activity of inhibiting release of leukotriene B$_4$ from rat macrophages was measured according to the following method for test samples consisting of Tomato Extract 1 obtained in Example 1-1, naringenin chalcone obtained in Example 1-3 and tricaffeoylquinic acid obtained in Example 1-4, and those results are shown in Table 2.

Soluble starch (Wako, grade 1) and Bactopeptone (Difco) were suspended in physiological saline (0.9% NaCl, Ohtsuka Pharmaceutical, Co.) to have a concentration of 5% each. After sterilizing with an autoclave (121° C., 20 minutes), the suspension was cooled down to room temperature. The suspension was administered by injection into rat abdominal cavity in an amount of 5 mL per 100 g of body weight under ether anesthesia (using a 21G needle).

Four days later, the rats were sacrificed by exsanguination from the carotid artery under ether anesthesia. After adequately exsanguinating the rats, the rats were sprayed with ethanol and placed in a clean bench. 25 mL of CMF-HBSS (Ca, Mg free HBSS) were injected into the abdominal cavity followed by adequately rubbing the abdomen. The rats were laparotimized using sterilized instruments, and the solution within the abdominal cavity was collected. The collected solution was filtered using three layers of gauze. The abdominal cavity was further washed with 25 mL of CMF-HBSS (Ca, Mg free HBSS), and the solution was collected in the same manner. The collected cells were washed three times with ice-cold 0.1% BSA-PBS, suspended in 10% FBS-RPMI1640 medium. The cell suspension was dispersed in a 6 cm Petri dish to have 4.5×10⁶ cells/3 mL/dish, and incubated for 2 hours in an incubator kept at 5% CO$_2$ and 37° C. Subsequently, the supernatant was discarded, the Petri dish was washed three times with PBS to rinse off non-adherent cells, and the cells adhered onto inside of the Petri dish were used as macrophages. After the macrophages were pre-incubated for 20 minutes in 1% FBS-RPMI1640 medium, zymosan opsoninized using rat serum was added thereto, and the mixture was cultured in an incubator kept at 5% $CO_2$ and 37° C. for a predetermined period of time. Incidentally, samples were added 30 minutes before addition of zymosan. After completion of culture, supernatant from the culture was recovered and the amount of $LTB_4$ in the supernatant was measured using an ELISA kit (Leukotriene $B_4$ EIA Kit, Cayman). Activity of inhibiting release of leukotriene $B_4$ was calculated from the measured leukotriene $B_4$ values using the following calculation formula (2):

$$\text{Leukotriene } B_4 \text{ release inhibition rate (\%)} = (1-(S-B)/(C-B))\times 100 \quad (2)$$

B: Amount of leukotriene $B_4$ released from control cells in the absence of inducer
C: Amount of leukotriene $B_4$ released from cells in the presence of inducer
S: Amount of leukotriene $B_4$ released from cells in the presence of test sample and inducer

TABLE 2

| Sample concentration (µg/ml) | | Inhibition rate (%) |
|---|---|---|
| Tomato Extract 1 | (1000 µg/ml) | 84.1 |
| Tomato Extract 1 | (500 µg/ml) | 64.4 |
| Tomato Extract 1 | (250 µg/ml) | 25.1 |
| Tricaffeoylquinic acid | (500 µg/ml) | 69.7 |
| Tricaffeoylquinic acid | (50 µg/ml) | 65.8 |
| Tricaffeoylquinic acid | (5 µg/ml) | 33.5 |
| Naringenin chalcone | (500 µg/ml) | 98.2 |
| Naringenin chalcone | (50 µg/ml) | 93.5 |
| Naringenin chalcone | (5 µg/ml) | 62.3 |

As is clear from the results shown in Table 2, tomato extract, naringenin chalcone and tricaffeoylquinic acid exhibited a leukotriene release inhibiting activity in a dose dependent manner.

Example 4

Evaluation of Anaphylaxis Inhibitory Action in Mouse Auricular Edema (1) Anaphylaxis inhibitory action was measured according to the method described below with respect to Tomato Extract 1 obtained in Example 1-1. Those results are shown in Table 3.

C3H/Hecrj, 7-week-old female mice having body weights of 15-20 g were used in groups of five animals each. Tomato Extract 1 was suspended in 0.5% CMC-Na (sodium carboxymethyl cellulose) solution, while 0.5% CMC-Na was administered as a control. The samples were administered six times over the course of five days, and measurements were made on day 5. The animals were dosed once a day from day 1 through day 4, and on day 5, they were orally dosed twice, 4 hours before and 30 minutes after administration of anti-TNP-IgE solution. The dose of Tomato Extract 1 was 0.16 mg, 0.8 mg or 4 mg per 1 kg of mouse body weight.

0.2 ml of 1% anti-TNP-IgE solution was administered from the vein of eye ground, and 30 minutes later, sample solution was orally administered. Further 30 minutes later, thickness of the left and right ears were measured. Immediately after that, 10 µl of 0.8% acetone-olive oil (1:1) solution of picryl chloride was applied to each ear. The thickness of the left and right ears of the mice were measured two hours after application, and the difference in ear thickness before and after application was taken to represent edema caused by anaphylaxis. A test of significance was carried out using the Student's t-test.

TABLE 3

| Groups | Anti-TNP-IgE antibody | Dose of Tomato Extract (mg/kg/dose) | Picryl chloride on ears | Edema (mm) ± SE |
|---|---|---|---|---|
| Tomato Extract | + | 4 | + | 0.975 ± 0.028** |
| Tomato Extract | + | 0.8 | + | 1.175 ± 0.064* |
| Tomato Extract | + | 0.16 | + | 1.350 ± 0.049 |
| Control group sensitized with picryl chloride | + | 0 | + | 1.555 ± 0.113 |
| Control group without sensitization | − | 0 | + | 0.142 ± 0.030 |

**$p < 0.01$ (significant difference from the control group sensitized with picryl chloride)
*$p < 0.05$ (significant difference from the control group sensitized with picryl chloride)

(2) Anaphylaxis inhibitory action was measured in the same manner as in the above-mentioned (1) with respect to the naringenin chalcone obtained in Example 1-3. The dose of naringenin chalcone was 0.0064 mg, 0.032 mg, 0.16 mg or 0.8 mg per kilogram of mouse body weight. The results are shown in FIG. 8.

Figure 8:
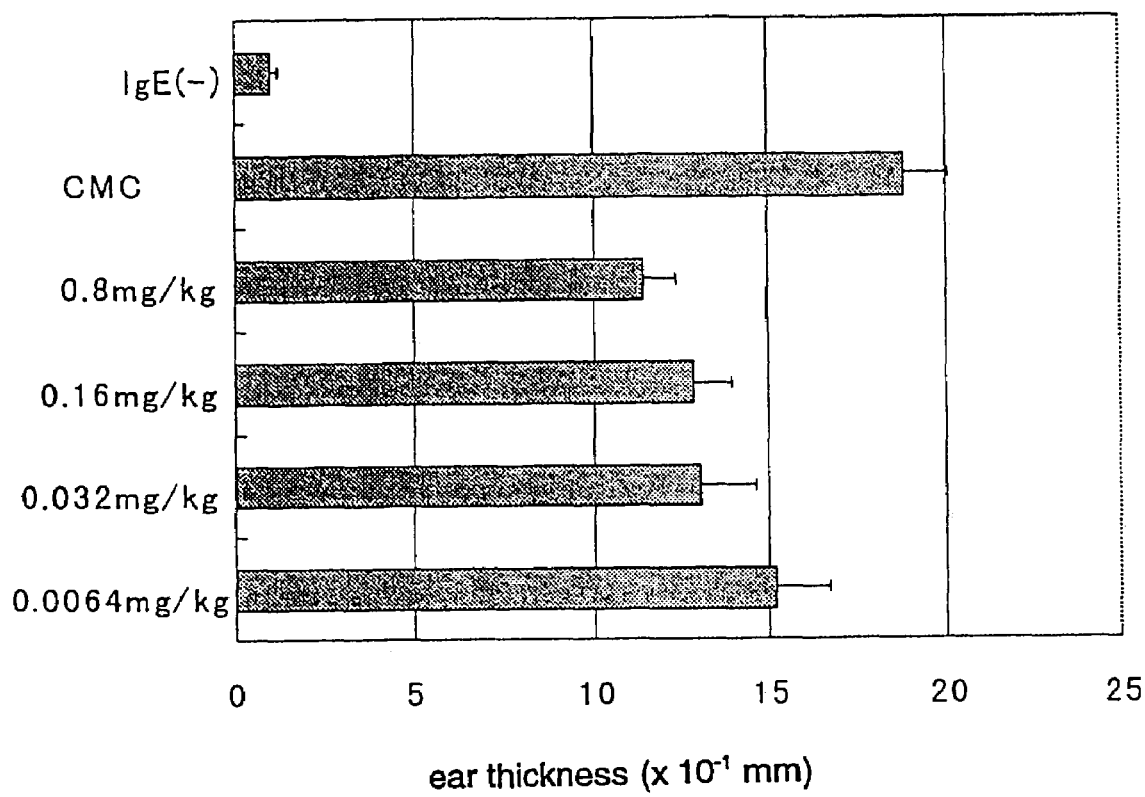
FIG. 8 shows an inhibitory action of naringenin chalcone on anaphylaxis in mouse auricle edema model.

As is clear from the results shown in FIG. 8, naringenin chalcone exhibited an anaphylaxis inhibitory action dose-dependently. Since anaphylaxis is a type of allergy symptom, naringenin chalcone was further indicated as being useful as an antiallergic agent.

(3) Anaphylaxis inhibitory action was measured in the same manner as in the above-mentioned (1) with respect to the tricaffeoylquinic acid obtained in Example 1-4. The dose of tricaffeoylquinic acid was 4 mg per kilogram of mouse body weight. The results are shown in FIG. 9.

Figure 9:
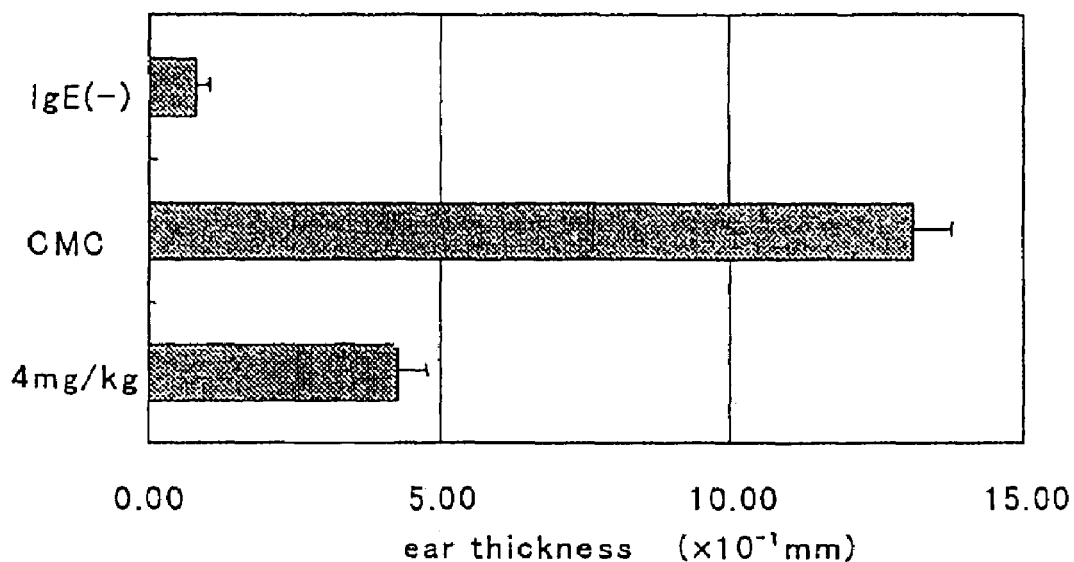
FIG. 9 shows an inhibitory action of tricaffeoylquinic acid on anaphylaxis in mouse auricle edema model.

As is clear from the results shown in FIG. 9, tricaffeoylquinic acid exhibited an anaphylaxis inhibitory action. Since anaphylaxis is a type I allergy symptom, tricaffeoylquinic acid was further indicated as being useful as an antiallergic agent.

(4) Anaphylaxis inhibitory action was measured using the method described below with respect to the tricaffeoylquinic acid obtained in Example 1-4. The results are shown in FIG. 10.

Measurement was made in the same manner as in (1) above, except for administration method. Samples were administered six times over the course of five days, and measurement was made on day 5. The animals were dosed once a day from day 1 through day 4, and on day 5, they were orally dosed twice, 4 hours before and 30 minutes after administration of anti-TNP-IgE solution. The dose of tricaffeoylquinic acid was 0.16 mg, 0.8 mg, 4 mg or 20 mg per kilogram of mouse body weight.

Figure 10:
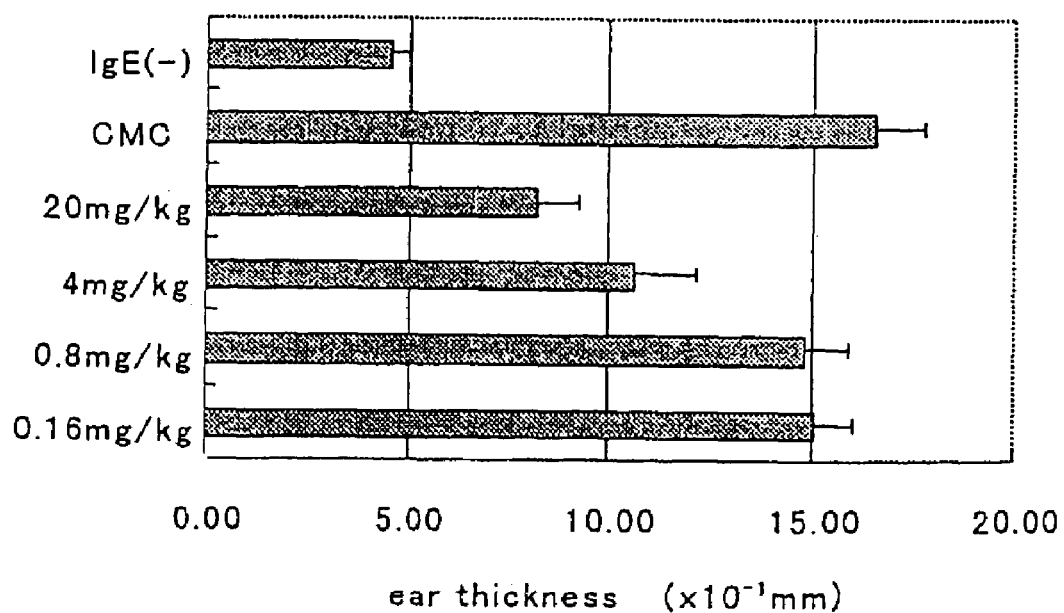
FIG. 10 shows an inhibitory action of orally administered tricaffeoylquinic acid on anaphylaxis in mouse auricle edema model.

As is clear from the results of FIG. 10, tricaffeoylquinic acid exhibited an anaphylaxis inhibitory action.

Example 5

Cytotoxicity Test

To 80 µl of cell suspension (1-2×10$^6$ cells/ml) prepared in the same manner as in Example 2 were added 20 µl of sample solutions (Tomato Extract 1, naringenin chalcone, tricaffeoylquinic acid or dicaffeoylsuccinylquinic acid obtained in Example 1) with various concentrations, and the mixture was cultured at 37° C. Each of 10 µl aliquots was taken after 0, 10, 20, 60 and 120 minutes from the start of culturing, and each aliquot was added to 20 µl of 0.4% Trypan Blue prepared in advance. Judging those cells that were stained with blue pigment to be dead cells, the number of cells was counted under microscopic examination using a hemocytometer. Viability (percentage of viable cells to the total number of cells) and the number of viable cells were measured. As a result, no cytotoxicity was observed.

Example 6

Medicament Comprising Antiallergic Agent of the Present Invention (1) Tomato Extract 1 (100 g) of Example 1-1 was mixed with an equal amount of lactose and 5 g of magnesium stearate, and the mixture was formed into tablets with a single-action tablet-making machine to produce tablets having a diameter of 10 mm and a weight of 300 mg.

(2) The tablets obtained in (1) above were then pulverized, graded and sized through a sieve to obtain granules of 20-50 mesh.

The naringenin chalcone purified in Example 1-3 was prepared in the manner described below to give a medicament.

(3) 100 g of naringenin chalcone was mixed with an equal amount of lactose and 5 g of magnesium stearate, and the mixture was formed into tablets with a single-action tablet-making machine to produce tablets having a diameter of 10 mm and a weight of 300 mg.

(4) The tablets obtained in (3) above were then pulverized, graded and sized through a sieve to obtain granules of 20-50 mesh.

The tricaffeoylquinic acid or dicaffeoylsuccinylquinic acid purified in Example 1-4 or Example 1-5 was prepared in the manner described below to give a medicament.

(5) An equal amount of lactose and 5 mg of magnesium stearate were mixed into 100 g of antiallergic agent, and this mixture was then formed into tablets with a single-action tablet-making machine to product tablets having a diameter of 10 mm and a weight of 300 mg.

(6) The tablets obtained in (5) above were pulverized, graded and sized through a sieve to obtain granules of 20-50 mesh.

Example 7

Foods and Drinks Comprising Antiallergic Agent of the Present Invention (7-1a) Candy with the following composition (parts by weight) was prepared.
Sugar (47.0), starch syrup (49.76), fragrance (1.0), water (2.0), and Tomato Extract 1 (0.24).

(7-1b) Candy with the following composition (parts by weight) was prepared as a food comprising an antiallergic agent of the present invention.
Sugar (47.0), starch syrup (49.76), fragrance (1.0), water (2.0), and naringenin chalcone (0.24).

(7-1c) Candy with the following composition (parts by weight) was prepared as a food comprising an antiallergic agent of the present invention.
Sugar (47.0), starch syrup (49.76), fragrance (1.0), water (2.0), and tricaffeoylquinic acid or dicaffeoylsuccinylquinic acid (0.24).

(7-2) Tomato juice with the following composition (parts by weight) was prepared.
Commercially available tomato juice (99) and Tomato Extract 1 (1.0) were mixed.

(7-3a) Juice with the following composition (parts by weight) was prepared.
Concentrated mandarin orange juice (5), fructose-glucose syrup (11), citric acid (0.2), L-ascorbic acid (0.02), Tomato Extract 1 (1.0), and water added in an amount to make the total 100 parts by weight.

(7-3b) Juice with the following composition (parts by weight) was prepared.
Concentrated mandarin orange juice (5), fructose-glucose syrup (11), citric acid (0.2), L-ascorbic acid (0.02), tricaffeoylquinic acid or dicaffeoylsuccinylquinic acid (0.1), and water added in such an amount to bring the total to 100 parts by weight.

Example 8

Cosmetics Comprising Antiallergic Agent of the Present Invention (8-1a) Toothpaste with the following composition (parts by weight) was prepared.
Calcium diphosphate (42), glycerin (18), carrageenan (0.9), sodium lauryl sulfate (1.2), sodium saccharin (0.09), butyl paraoxybenzoate (0.005), Tomato Extract 1 (1.0), fragrance (1), and water added in such an amount to bring the total to 100 parts by weight.

(8-1b) Toothpaste with the following composition (parts by weight) was prepared.
Calcium diphosphate (42), glycerin (18), carrageenan (0.9), sodium lauryl sulfate (1.2), sodium saccharin (0.09), butyl paraoxybenzoate (0.005), naringenin chalcone (0.05)., fragrance (1), and water added in such an amount to bring the total to 100 parts by weight.

(8-1c) Toothpaste was produced having the composition (parts by weight) indicated below.
Calcium diphosphate (42), glycerin (18), carrageenan (0.9), sodium lauryl sulfate (1.2), sodium saccharin (0.09), butyl paraoxybenzoate (0.005), tricaffeoylquinic acid or dicaffeoylsuccinylquinic acid (0.1), fragrance (1), and water added in such an amount to bring the total to 100 parts by weight.

(8-2a) Skin lotion with the following composition (parts by weight) was prepared.
Glycerin (5.0), propylene glycol (4.0), tomato extract (0.5), polyoxyethylenesorbitan monolaurate ester (2.0), ethanol (10.0), fragrance (0.1) and purified water added in such an amount to bring the total to 100 parts by weight.

(8-2b) Skin lotion with the following composition (parts by weight) was prepared.
Glycerin (5.0), propylene glycol (4.0), naringenin chalcone (0.15), polyoxyethylenesorbitan monolaurate ester (2.0), ethanol (10.0), fragrance (0.1) and purified water added in such an amount to bring the total to 100 parts by weight (8-2c) Skin lotion with the following composition (parts by weight) was prepared.

Glycerin (5.0), propylene glycol (4.0), tricaffeoylquinic acid or dicaffeoylsuccinylquinic acid (0.3), polyoxyethylenesorbitan monolaurate ester (2.0), ethanol (10.0), fragrance (0.1) and purified water added in such an amount to bring the total to 100 parts by weight.

(8-3a) Hair rinse with the following composition (parts by weight) was prepared.

Dimethyl stearyl chloride (1.4), benzylammonium stearyl alcohol (0.6), glycerin monostearate (1.5), table salt (0.1), Tomato Extract 1 (0.5) and purified water added in such an amount to bring the total to 100 parts by weight.

(8-3b) Hair rinse with the following composition (parts by weight) was prepared.

Dimethyl stearyl chloride (1.4), benzylammonium stearyl alcohol (0.6), glycerin monostearate (1.5), table salt (0.1), naringenin chalcone (0.1) and purified water added in such an amount to bring the total to 100 parts by weight.

(8-3c) Hair rinse with the following composition (parts by weight) was prepared.

Dimethyl stearyl chloride (1.4), benzylammonium stearyl alcohol (0.6), glycerin monostearate (1.5), table salt (0.1), antiallergic agent (0.1) and purified water added in such an amount to bring the total to 100 parts by weight.

INDUSTRIAL APPLICABILITY

According to the present invention, antiallergic agents comprising, as an active ingredient, tomato extract, naringenin chalcone or its derivatives, and/or tricaffeoylquinic acid or dicaffeoylsuccinylquinic acid or their derivatives, antiallergic agents comprising tomato pericarp as an active ingredient, and a method for producing an antiallergic agent comprising a step of extracting raw material tomato with a solvent, are provided.

For the raw material tomato to be extracted, tomato pericarp and squeezed tomato residue can be used. These are waste materials produced in large amounts at the food-processing sites of tomato juice, ketchup and the like. The present invention is extremely useful also in the sense that these industrial wastes can be effectively utilized.

Since the antiallergic agents of the present invention exhibit an excellent histamine-release inhibitory activity and an excellent leukotriene-release inhibitory activity, they are useful as preventive and therapeutic agents, anti-inflammatory agents, or as histamine-release inhibitors or leukotriene-release inhibitors, for various allergic diseases. In addition, since the antiallergic agents of the present invention inhibit the histamine-release from fat cells in type I allergic reactions, they are particularly useful in the prevention and treatment of atopic dermatitis, allergic rhinitis, pollinosis or allergic asthma and so forth caused thereby.

In addition, medicaments, foods, drinks and cosmetics which comprise said antiallergic agents are provided by the present invention. The antiallergic agents of the present invention are able to impart an antiallergic activity, anti-inflammatory activity or histamine-release inhibitory activity to medicaments, foods, drinks and cosmetics by adding them to these products.

The invention claimed is:

1. A method of treating allergies or an allergic reaction, said method comprising:

administering an effective amount of a pharmaceutical composition comprising at least two isolated or purified compounds selected from the group consisting of a naringenin chalcone, a tricaffeoylquinic acid and a dicaffeoylsuccinylquinic acid as active ingredients or a pharmacologically acceptable salt or ester of any of said active ingredients to a patient in need thereof, wherein said active ingredients are administered in a total amount of about 0.1 to 1,000 mg per day, wherein said allergy or allergic reaction is at least one selected from the group consisting of atopic dermatitis, allergic rhinitis, pollinosis, allergic asthma and a food allergy.

2. A method of treating allergies or an allergic reaction, said method comprising:

administering to a subject in need thereof a food, drink or cosmetic comprising an effective amount of at least two isolated or purified compounds selected from the group consisting of a naringenin chalcone, a tricaffeoylquinic acid and a dicaffeoylsuccinylquinic acid as active ingredients or a salt or ester of any of said active ingredients, wherein said active ingredients are administered in a total amount of about 0.1 to 1,000 mg per day, wherein said allergy or allergic reaction is at least one selected from the group consisting of atopic dermatitis, allergic rhinitis, pollinosis, allergic asthma and a food allergy.

3. The method of claim 2, in which a cosmetic is topically applied to the skin of said subject.

4. The method of claim 1, wherein said pharmaceutical composition is in the form of a tablet, granule, powder, syrup, suppository or external preparation.

5. The method of claim 1, wherein said pharmaceutical composition comprises isolated or purified tomato pericarp.

* * * * *

UNITED STATES PATENT AND TRADEMARK OFFICE
CERTIFICATE OF CORRECTION

PATENT NO. : 7,511,078 B2  Page 1 of 1
APPLICATION NO. : 10/312504
DATED : March 31, 2009
INVENTOR(S) : Taichi Yamamoto et al.

It is certified that error appears in the above-identified patent and that said Letters Patent is hereby corrected as shown below:

Column 3, line 50:
"to s size of 16 mesh or finer." should read --to a size of 16 mesh or finer.--

Column 17, line 53:
"to product tablets" should read --to produce tablets--

Column 18, line 46:
"naringenin chalcone (0.05).," should read --naringenin chalcone (0.05),--

Signed and Sealed this

Ninth Day of February, 2010

David J. Kappos
*Director of the United States Patent and Trademark Office*